United States Patent [19]

Rose et al.

[11] Patent Number: 4,627,879
[45] Date of Patent: Dec. 9, 1986

[54] FIBRIN ADHESIVE PREPARED AS A CONCENTRATE FROM SINGLE DONOR FRESH FROZEN PLASMA

[75] Inventors: Eric Rose, Palisades, N.Y.; Arthur Dresdale, Plainfield, N.J.

[73] Assignee: The Trustees of Columbia University in the City of New York, New York, N.Y.

[21] Appl. No.: 688,601

[22] Filed: Jan. 3, 1985

Related U.S. Application Data

[63] Continuation-in-part of Ser. No. 648,752, Sep. 7, 1984, abandoned.

[51] Int. Cl.$^4$ .................. A61B 17/04; A61F 13/00; A61K 37/00; C08L 89/00
[52] U.S. Cl. .................. 106/124; 106/161; 128/334 R; 424/28; 424/101; 514/2; 514/802
[58] Field of Search .................. 424/28, 101, 177; 514/802, 2; 106/124, 161; 128/334 R

[56] References Cited

U.S. PATENT DOCUMENTS

| | | | |
|---|---|---|---|
| 2,112,496 | 3/1938 | Ide et al. | 436/511 |
| 4,362,567 | 12/1982 | Schwarz et al. | 106/124 |
| 4,383,989 | 5/1983 | Rock | 424/101 |
| 4,414,976 | 11/1983 | Schwarz et al. | 106/124 |
| 4,427,650 | 1/1984 | Stroetmann | 424/101 |
| 4,427,651 | 1/1984 | Stroetmann | 424/101 |
| 4,449,938 | 5/1984 | Pollak | 523/116 |

*Primary Examiner*—Theodore Morris
*Attorney, Agent, or Firm*—John P. White

[57] ABSTRACT

This invention concerns a method of preparing a cryoprecipitated suspension containing fibrinogen and Factor XIII useful as a precursor in the preparation of a fibrin glue which involves (a) freezing fresh frozen plasma from a single donor such as a human or other animal, e.g. a cow, sheep or pig, which has been screened for blood transmitted diseases, e.g. one or more of syphilis, hepatitis or acquired immune deficiency syndrome at about =80° C. for at least about 6 hours, preferably for at least about 12 hours; (b) raising the temperature of the frozen plasma, e.g. to between about 0° C. and room temperature, so as to form a supernatant and a cryoprecipitated suspension containing fibrinogen and Factor XIII; and (c) recovering the cryoprecipitated suspension.

The invention also concerns a method of preparing a fibrin glue useful in surgical procedures which comprises: (a) preparing a cryoprecipitated suspension as described above; (b) applying a defined volume of the suspension to a desired site; and (c) applying a composition containing a sufficient amount of thrombin, e.g. human, bovine, ovine or porcine thrombin, to the site so as to cause the fibrinogen in the suspension to be converted to the fibrin glue which then solidifies in the form of a gel.

The thrombin-containing composition may also contain a suitable amount of an anti-fibrinolytic substance, e.g. aprotinin and a suitable amount of $CaCl_2$.

The invention also concerns the cryoprecipitated suspension, the fibrin glue formed therefrom, fibrin glue kits and a method for sealing surgical wounds.

21 Claims, 1 Drawing Figure

FIBRIN ADHESIVE PREPARED AS A CONCENTRATE FROM SINGLE DONOR FRESH FROZEN PLASMA

BACKGROUND OF THE INVENTION

This application is a continuation-in-part of U.S. Ser. No. 648,752, filed Sept. 7, 1984, now abandoned, the contents of which are hereby incorporated by reference into the present application.

Within this application several publications are referenced by arabic numerals within parentheses. Full citations for these references may be found at the end of the specification immediately preceding the claims. The disclosures of these publications in their entireties are hereby incorporated by reference into this application.

A major technical advance in surgery underutilized in this country has been the clinical application of fibrin glue. Clinical reports (1,3,8,9,10,12,14,16,17) document the utility of this concentrated adhesive, which duplicates the biological process of the final stage of normal coagulation (FIG. 1). Fibrin glue has been used to control bleeding from liver lacerations and traumatized spleens (3,14). Other uses include sealing sewn or stapled tracheal and esophageal anastomoses as well as persistent air leaks or lacerations of the lung (1,12). Bronchial fistulas have been successfully closed using fibrin adhesive. A useful application has been in vascular surgery. An important feature is its ability to achieve hemostasis at vascular anastomoses particularly in areas which are difficult to approach with sutures or where suture placement presents excessive risk (1,10,12,16). Bleeding from needle holes or small arterial tears which cannot be controlled by suturing alone usually can be sealed by judicious fibrin glue application (1). It has been especially helpful in obtaining hemostasis in heparinized patients or those with coagulopathy (1,17). Furthermore, fibrin glue impregnation permits the use of porous knitted grafts, even in anticoagulated patients, eliminating bleeding which has prevented the widespread use of these porous grafts in open heart surgery (1,8,9,16).

Various techniques have been described to pretreat porous vascular prostheses. Many are complicated, time consuming, expensive procedures and often render prostheses stiff and non-yielding (7,18). A previously described highly effective method using a cryoprecipitate preparation (6) was criticized because of its high cost (11).

Haverich et al. (8) reported that fibrin presealing allows the use of high porosity knitted Dacron prostheses even in heparinized patients. A highly porous fabric, with its superior healing characteristics, offers the potential for a lower incidence of right ventricular conduit obstruction (8). Fibrin presealed grafts are no more thrombogenic, and may be less so, than untreated grafts or those pretreated with blood (9,18). Highly porous fabrics have superior handling characteristics compared to low porosity grafts, and the use of fibrin adhesive could make low porosity woven Dacron grafts obsolete.

Despite generalized acceptance and use in Europe as a tissue sealant and hemostatic agent, fibrin glue has received little attention in the United States. In large part, this stems from the 1978 U.S. Food and Drug Administration ban (13) on the sale of commercially prepared fibrinogen concentrate made from pooled donors, e.g., as in Schwarz, et al., U.S. Pat. Nos. 4,298,598 (1981), 4,362,567 (1982) or 4,414,976 (1983), because of the risk of transmission of viral infection, in particular hepatitis B (2). In addition, the recent appearance of Acquired Immune Deficiency Syndrome also a major health concern, makes it unlikely that there will be a change in this policy in the foreseeable future (4).

Concentrated fibrinogen can be prepared with minimal risk of disease transmission from a patient's own blood (5,19). Although this technique obviously eliminates the risk of blood transmitted viral infection, it requires anticipating surgery at least two days in advance so that the autologous blood can be drawn and prepared in time. In addition, it requires the patient to donate at least one unit of blood and may result in the need for blood transfusion to replace donated blood. Furthermore, it is not practical to depend on autologous blood as a source for fibrin adhesive in trauma cases and other unanticipated surgical emergencies. This invention concerns a convenient and practical method of preparing fibrinogen and fibrin glue which avoids the risk of transmission of disease in contrast to prior methods, e.g., the method of Schwarz, et al. This method makes available an abundance of fibrinogen concentrate safe for use within minutes whenever needed in the operating room.

SUMMARY OF THE INVENTION

This invention concerns a method of preparing a cryoprecipitated suspension containing fibrinogen and Factor XIII useful as a precursor in the preparation of a fibrin glue. The method involves (a) freezing fresh frozen plasma from a single donor, e.g. a human or other animal such as a cow, pig or sheep, which has been screened for blood transmitted diseases, e.g. one or more of syphilis, hepatitis or acquired immune deficiency syndrome at about −80° C. for at least about 6 hours, preferably for at least about 12 hours; (b) raising the temperature of the frozen plasma, e.g. to about 0° C. to about room temperature, preferably to about 4° C., so as to form a supernatant and a cryoprecipitated suspension containing fibrinogen and Factor XIII; and (c) recovering the cryoprecipitated suspension, e.g. by decanting the supernatant. The suspension may be concentrated, e.g., by centrifugation.

This invention further concerns the cryoprecipitated suspension containing fibrinogen and Factor XIII so prepared, which additionally may be pre-formed and stored frozen.

The invention also concerns a method of preparing a fibrin glue useful in surgical procedures which involves (a) preparing a cryoprecipitated suspension as described above; (b) applying a defined volume of the suspension to a desired site; and (c) applying a composition containing a sufficint amount of thrombin from an appropriate source, e.g. human, bovine, ovine or porcine thrombin, to the site so as to cause the fibrinogen in the suspension to be converted to the fibrin glue which then solidifies in the form of a gel.

The thrombin-containing composition may also contain a suitable amount of an anti-fibrinolytic substance, such as aprotinin and may also contain $CaCl_2$.

The suspension and the composition containing thrombin may be applied to the site in a surgically acceptable vehicle such as a gel, e.g. gelatin or a stretched fabric.

The invention further concerns a method of sealing a surgical wound which involves applying to the wound a suitable amount of a cryoprecipitated suspension prepared in accordance with this invention and applying a composition containing thrombin to the site so as to cause the fibrinogen in the suspension to be converted to a fibrin glue which then solidifies in the form of a gel. Pressure may be applied to the fibrin glue until it solidifies. The suspension and composition may be applied in a surgically acceptable vehicle such as a gel. Alternately, they may be applied in a stretched fabric such as a synthetic vascular patch or graft.

Additionally, this invention involves a fibrin glue kit for use in providing hemostasis during surgery. The kit contains the above-mentioned cryoprecipitated suspension and a composition containing thrombin. The thrombin-containing composition may additionally contain a suitable amount of an anti-fibrinolytic substance, e.g. aprotinin, and may also contain a suitable amount of an appropriate calcium salt, e.g. $CaCl_2$. The kit may further contain at least one synthetic vascular graft or patch.

DETAILED DESCRIPTION OF THE INVENTION

Figure 1:
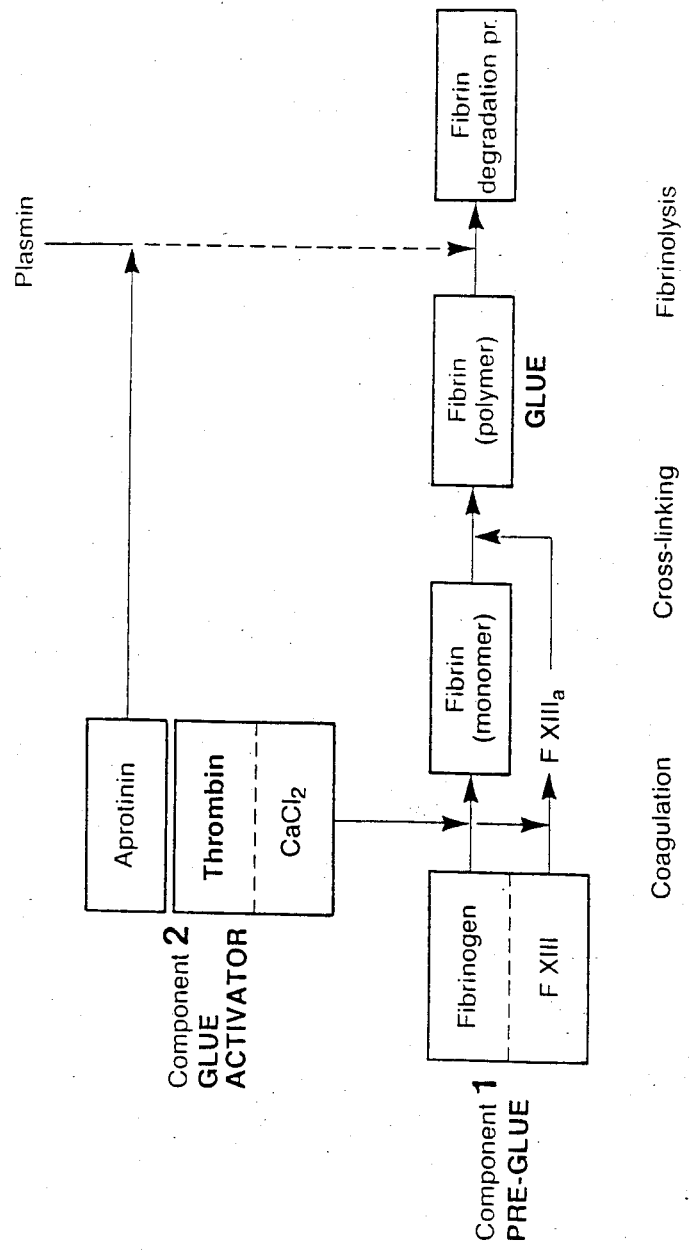
FIG. 1: The use of fibrin adhesive exploits the final stage of coagulation cascade. The first component which is prepared from fresh frozen plasma (FFP) by cryoprecipitation contains fibrinogen and Factor XIII (FXIII) and is labeled "PREGLUE". The second component, labeled "GLUE ACTIVATOR" contains thrombin and may additionally contain Aprotinin and $CaCl_2$.

As mentioned above, this invention concerns a method of preparing a cryoprecipitated suspension containing fibrinogen and Factor XIII useful as a precursor in the preparation of a fibrin glue which comprises:

(a) freezing fresh frozen plasma from a single donor which has been screened for blood transmitted diseases such as one or more of syphilis, hepatitis or acquired immune deficiency syndrome at about $-80°$ C. for at least about 6 hours, preferably for at least about 12 hours;

(b) raising the temperature of the frozen plasma to between about 0° C. and room temperature, preferably about 4° C., so as to form a supernatant and a cryoprecipitated suspension containing fibrinogen and Factor XIII; and (c) recovering the cryoprecipitated suspension.

In a preferred embodiment the cryoprecipitated suspension is prepared in 50 cc polypropylene centrifuge tubes (Fisher Scientific, Springfield, NJ) which have been charged with screened, fresh frozen plasma (FFP) from a single donor. The single donor may be a human or an animal, e.g. a cow, sheep, pig, goat, rabbit, guinea pig, rat or mouse so long as the cryoprecipitated suspension is capable of reacting with thrombin from an appropriate source to produce fibrin glue, as disclosed herein. Preferably the fresh frozen plasma is bovine, ovine or porcine. The tubes are then placed in a freezer at $-80°$ C. for at least twelve hours, and the fibrinogen-containing suspension prepared for use or storage by thawing over several hours at 4° C. The tubes containing the thawed fibrinogen-containing suspension are then centrifuged, e.g., at about $1000-2300 \times G$ for fifteen to twenty minutes preferably in a refrigerated centrifuge. The supernatant is decanted leaving a yellowish precipitate containing fibrinogen. The precipitated and centrifuged pellet of concentrated fibrinogen is resuspended in the small amount of supernatant remaining after decantation.

Since the final concentration of fibrinogen is partly determined by the volume of residual supernatant which is used to resuspend the fibrinogen pellet, this maneuver is performed with care so as to remove as much liquid as possible without disturbing the pellet. Next, the concentrated fibrinogen suspension is aspirated into a syringe using a large bore spinal needle. The total yield is approximately 2 cc's of concentrated fibrinogen from each 40 cc's of FFP. Measured fibrinogen in this concentrate is 2160 mg% compared to 260 mg% in the virgin FFP (see Table I). Factor XIII also is present in the final preparation. All aspects of the procedure are performed in a laminar flow hood under sterile conditions and the final product is checked for contamination by routine culture.

The concentrated fibrinogen-containing cryoprecipitated suspension may be prepared well in advance of its intended use, i.e., pre-formed, and stored for up to two months at $-80°$ C. before use. Reports indicate it can be stored for as long as one year (5). After thawing, it reportedly can be kept for three to four days at 4° C., but we have found it retains biological activity for as long as two weeks. Once at room temperature, the concentrate should be used within four hours (5).

TABLE I

Fibrinogen, Factor XIII, and Fibrin Split Product Levels in Representative Samples of Fresh Frozen Plasma and Whole Blood

| Sample | FSP (g/ml) | Factor XIII | Fibrinogen (mg %) |
|---|---|---|---|
| FFP-A[1] | — | present | 260 |
| FFP-A[2] | 0 | present | 2160 |
| Whole Blood[3] | 0 | present | 2160 |

[1]A sample of FFP was thawed only and then tested without cryoprecipitation treatment.
[2]Cryoprecipitate of sample A revealing almost a 10 fold increase of concentration.
[3]Unit of single donor whole blood obtained from Presbyterian Hospital Blood Bank where it had been stored for several days at 1–4° C.

This invention further involves a method of preparing a fibrin glue useful in surgical procedures which comprises: (a) preparing a cryoprecipitated suspension as described above; (b) applying a defined volume of the suspension to a desired site; and (c) applying a composition containing a sufficient amount of thrombin to the site so as to cause the fibrinogen in the suspension to be converted to the fibrin glue which then solidifies in the form of a gel.

Suitable thrombin for use in this invention may be derived from a human or an animal, e.g. a cow, sheep or pig and includes e.g. human, porcine or bovine thrombin such as commercial bovine thrombin, e.g. Thrombinar ® (Armour Pharmaceutical Co., Kankakee, IL). The thrombin-containing composition may also contain a suitable amount of an anti-fibrinolytic substance, e.g. aprotinin, and a suitable amount of an appropriate calcium salt, e.g. $CaCl_2$.

In a preferred embodiment the glue is prepared as follows: the cryoprecipitated suspension containing fibrinogen and Factor XIII and commercial bovine thrombin (Thrombinar ® Armour Pharmaceutical Co., Kankakee, IL) are placed into separate one cc syringes. A defined volume of the fibrinogen-containing cryoprecipitated suspension is applied to a desired site. The composition containing a sufficient amount of thrombin is then applied to the site so as to cause the fibrinogen in the suspension to be converted to the fibrin glue which then solidifies in the form of a gel. With a thrombin mixture of 500 units/ml, the fibrinogen gels into a fibrin clot in less than one minute. The glue works most effectively when applied in a relatively dry field. For example, application to a vascular suture line several minutes prior to clamp removal allows time for the glue to congeal. A transparent gel-like film adheres to the suture line and results in hemostasis after the clamps are released. In a wet field, the suspension and the composition containing thrombin may be applied to the site in a surgically acceptable vehicle. In a wet field a vehicle comprising a gel such as gelatin, e.g. Gelfoam ® (Upjohn Co.), or microfibrillar collagen wafers (collagen fleece) e.g. Avitine ® (Alcon, Inc., Humacao, Puerto Rico) is preferred. Preferably the collagen is bovine, ovine or porcine collagen. In the former embodiment the gel is saturated with thrombin and then impregnated with the fibrinogen. The Gelfoam ® acts as a vehicle to hold the fibrin while clotting occurs. To control active bleeding, the glue should be applied on thrombin soaked Gelfoam ® and digital pressure exerted over the site of bleeding for one minute while the glue sets. Care must be taken to avoid suctioning directly over the area of glue application because this may result in aspirating not only blood, but also soluble glue before it has polymerized.

To pretreat porous vascular grafts, the technique described by Borst (1) may be employed using a vehicle comprising a stretched fabric. In this embodiment several milliliters of the fibrinogen concentrate is spread over the outer surface of the stretched fabric. Following thorough coating of the graft, the thrombin activating solution is massaged into the graft. After the graft is inserted, a few additional drops of glue are applied directly over needle holes before clamp removal. Porous grafts, so pretreated, offer advantages in handling, suturing and long-term patency.

As with any technique, successful use of fibrin glue depends on proper application gained through experience. Our adhesive has stopped bleeding around vascular anastomoses, particularly needle holes and small linear tears, in a variety of situations involving aortotomies, reversed saphenous vein graft aortic and coronary artery anastomoses, and right ventricular conduit suture lines. By helping to control difficult bleeding, the use of fibrin glue in accordance with this invention can decrease the need for blood transfusions, shorten operating room time and may even be lifesaving. We have found that as experience is gained with the glue the list of potential uses is expanding.

Fibrin glue can be prepared from single donor FFP in sufficient quantity to meet surgical demand because the ease of extraction permits making large amounts of the glue. It can be stored for long periods of time at $-80°$ C. or for shorter periods of time at 4° C. until it is needed. By the method of this invention, it is not necessary to anticipate an operation days in advance in order to have fibrin glue available. It has become our practice to maintain a supply of glue at 4° C. for immediate use. This stock is checked and updated periodically.

One unit of FFP yields eight to ten cc's of concentrated fibrinogen. This represents enough glue to use in several operations. Approximately two or three cc's of concentrated cryoprecipitated suspension containing the fibrinogen combined with an equal volume of thrombin is adequate to preseal a right ventricular conduit. As little as one cc of glue effectively achieves hemostasis of bleeding suture lines or needle holes. In comparison, when fibrinogen is prepared from autologous whole blood, a smaller volume is extracted (approximately one cc for every one hundred cc's of whole blood) and it is limited to the volume of blood donated by that individual.

Moreover, the method of this invention of preparing the cryoprecipitated fibrinogen-containing suspension and the fibrin glue is easy to learn, reproducible, and economical. Most importantly, the use of single donor FFP entails no greater risk of transmission of Hepatitis B, Acquired Immune Deficiency Syndrome, and other serologically transmitted illness than transfusion of a unit of fresh frozen plasma. This decreased risk of blood born infection should circumvent the risk of blood transmitted diseases which led to the FDA proscription against preparing fibrin concentrate from pooled donors. Fibrin glue in accordance with this invention could become as readily available in this country as the preparation from pooled blood has been in Europe.

Comparison of fibrinogen prepared from autologous whole blood with the lyophilized, commercial European product (Tissucol ®, Immune AG, Vienna, Austria) indicates the tear coefficient of the latter is stronger (5). Unlike Tissucol ®, one embodiment of the present invention lacks antifibrinolytic additives and calcium chloride in the activating solution. The tenfold concentration of fibrinogen and presence of assayable Factor XIII indicate the hemostatic potency of our preparation. When used as a hemostatic agent or graft sealant, the FFP-derived glue functions so well that its adhesive properties are clear and unequivocal.

The cryoprecipitate of this invention can be included in a fibrin glue kit which also includes a composition containing thrombin. The thrombin-containing composition may additionally includes a suitable amount of an appropriate calcium salt such as $CaCl_2$ or an antifibrinolytic substance such as aprotinin or both. The kit may also include a surgically acceptable vehicle for the fibrin glue, such as a gel, or at least one synthetic vascular graft or patch or both. In particular, highly porous knitted grafts which appear to have long term patency rates superior to other types of grafts, but cannot presently be used in anti-coagulated patients (because of uncontrollable life threatening bleeding) could become widely utilized through this technique and may be included in a fibrin glue kit of this invention. It also may be possible to employ smaller synthetic fabric grafts in peripheral vascular surgery, currently not used because of high occlusion rates.

The methods, materials or kits of this invention may be used for sealing a surgical wound by applying to the wound a suitable amount of a cryoprecipitated suspension of this invention and applying a composition containing thrombin to the site so as to cause the fibrinogen in the suspension to be converted to a fibrin glue which then solidifies in the form of a gel. Pressure may be applied to the fibrin glue until it solidifies. The suspension and composition may be applied in a surgically acceptable vehicle, e.g. a gel. They may also be applied in a stretched fabric such as a synthetic vascular graft or patch. Uses for the methods, materials or kits of this invention in vascular surgery include providing hemostasis for stitch hole bleeding of distal coronary artery anastomoses; left ventricular suture lines; aortotomy and cannulation sites; diffuse epimyocardial bleeding seen in reoperations; and oozing from venous bleeding sites, e.g. at atrial, caval, or right ventricular levels. The invention is also useful for stopping bleeding from damaged spleens (thereby saving the organ), livers, and other parynchymatous organs; sealing tracheal and bronchial anastomoses and air leaks or lacterations of the lung; sealing bronchial stumps, bronchial fistulas and esophageal fistulas; for sutureless seamless healing ("Zipper" technique), and embolization in vascular radiology of intracerebral AVM's, liver AVM's, angiodysplasia of colon, esophageal varices, "pumping" GI bleeders secondary to peptic ulcers, etc. This invention is further useful for providing hemostasis in corneal transplants, nosebleeds, post tonsillectomies, teeth extractions and other applications.

EXAMPLE 1

Preparation of Cryoprecipitated Suspension (Pre-Glue)

FFP or citrated whole blood is obtained at least about 18 hours before intended use of Pre-glue. If whole blood is used as the starting material, it is first centrifuged at 2300×G for 5 min in 50 ml polypropylene centrifuge tubes (Fisher Scientific, Springfield, NJ). The plasma is then aspirated carefully, so as not to disturb the buffy coat or RBC layer. The plasma so prepared or FFP is then frozen at −80° C. for at least 12 hours. The frozen plasma is then thawed slowly at 4° C. (or at room temperature, though 4° C. is preferable). After thawing the tubes are centrifuged again at 2300×G for 20 minutes in a refrigerated centrifuge to separate the fluffy cryoprecipitate. The tubes are removed from the centrifuge carefully, so as not to resuspend the pellet. The supernatant is carefully decanted. Tapping the tubes resuspends the cryoprecipitate in the remaining plasma. The pellet, which contains fibrinogen and FXIII, is thick and yellow, and is aspirated into a syringe with a spinal needle for use or transfer to storage. All equipment used in the above-described example must be sterile.

EXAMPLE 2

Preparation of Fibrin Glue

A drop of the cryoprecipitated suspension prepared as in Example 1 is placed at the desired site. An amount of a composition containing reconstituted thrombin (e.g. Thrombinar ®, Armour Pharmaceutical Co., Kankakee, IL) appropriate to the amount of fibrinogen used is then added to the desired site. The thrombin causes the fibrinogen to be converted into the fibrin glue which solidifies in the form of a gel in less than one minute.

EXAMPLE 3

Preparation of Bovine Cryoprecipitated Suspension (Bovine Pre-Glue)

Example 1 may be repeated using fresh frozen bovine plasma or citrated bovine whole blood instead of human FFP or citrated human whole blood. Bovine pre-glue may be thereby obtained.

EXAMPLE 4

Preparation of Bovine Fibrin Glue

Example 2 may be repeated using bovine pre-glue prepared as in Example 3 in place of cryoprecipitated suspension of Example 1.

EXAMPLE 5

Use of Fibrin Glue without Anti-Fibrinolytic Additives

Fibrin glue prepared by the method of Example 2 was used to cover exposed saphenous vein grafts in a patient with a sternal wound infection which was treated with open drainage. The glue was monitored and was still in place 48 hours after application. The patient had received multiple wet to dry dressing changes and water pick irrigations of the wound without dislodgement of the glue. No evidence of gross fibrinolysis, e.g. late bleeding, was observed. Since the glue was formed without an antifibrinolytic additive such as aprotinin, such additives do not appear to be essential.

References

1. Borst H. G., Haverich A., Walterbusch G., Maatz W.: Fibrin Adhesive: an important hemostatic adjunct in cardiovascular operations. J. Thorac. Cardiovasc. Surg. 84: 548–553 (1982).
2. Bove J. R.: Fibrinogen—Is the benefit worth the risk? Transfusion 18: 129–136 (1978).
3. Brands W., Mennicken C., Beck M.: Preservation of the ruptured spleen by gluing with highly concentrated human fibrinogen: Experimental and clinical results. World J. Surg. 6: 366–368 (1982).
4. Conte J. E., Hadley W. K., Sande M., The University of California, San Francisco, Task Force on the Acquired Immunodeficiency Syndrome: Infection-control guidelines for patients with the acquired immunodeficiency syndrome (AIDS). N. Engl. J. Med. 309: 740–744 (1983).
5. Gestring G. F., Lerner R.: Autologous fibrinogen for tissue adhesion, hemostasis and embolization. Vascular Surgery 17: 294–304 (1983).
6. Glynn M. F. X., William W.: A technique for preclotting vascular grafts. Ann. Thorac. Surg. 29: 182–183 (1980).
7. Guidoin R., Snyder R., Martin L., Botzko K., Marois M., Awad J., King M., Domurado D., Bedros M., Gosselin C.: Albumin coating of a knitted polyester arterial protheses: An alternative to preclotting. Ann. Thorac. Surg. 37: 457–465 (1984).
8. Haverich A., Oelert H., Maatz W., Borst H. G.: Histopathological evaluation of woven and knitted dacron grafts for right ventricular conduits: A comparative experimental study. The Annals of Thoracic Surg. 37: 404–411 (1984).
9. Haverich A., Walterbusch G., and Borst H. G.: The use of fibrin glue for sealing vascular prostheses of high porosity. Thorac. Cardiovasc. Surgeon 29: 252–254 (1981).
10. Kalmar P., Krebber H. J., Pokar H., Tilsner V.: Bioadhesive in cardiac and vascular surgery. Thorac. Cardiovasc. Surg. 30: 230–231 (1982).
11. Kratz J. M.: Preclotting vascular grafts (Correspondence). Ann. Thorac. Surg. 31: 97 (1981).
12. Meisner H., Struck E., Schmidt-Habelman P., Sebening F.: Fibrin seal application. Clinical experience. Thorac. Cardiovasc. Surg. 30: 232–233 (1982).
13. Revocation of Fibrinogen Licenses: FDA Drug Bulletin 8: 15 (1978).
14. Scheele J., Gentsch H. H., Matheson E.: Splenic repair by fibrin tissue adhesive and collagen fleece. Surgery 95: 6–13 (1984).

15. Thurer R. L., Hauer J. M., Weintraub R. M.: A comparison of preclotting techniques for prosthetic aortic replacement. Circulation 66: I-143- I-146 (1982).

16. Walterbusch G., Haverich A., Borst H. G.: Clinical experience with fibrin glue for local bleeding control and sealing of vascular prostheses. Thorac. Cardiovasc. Surg. 30: 234–235 (1982).

17. Wolner E.: Fibrin gluing in cardiovascular surgery. Thorac. Cardiovasc. Surg. 30: 236–237 (1982).

18. Yates S. G., Aires M. S., Barros D'SA M. B., Berger K., Fernandez L. G., Wood S. J., Rittenhous E. A., Davis C. C., Mansfield P. B., Sauvage L. R.: The preclotting of porous arterial prostheses. Ann. Surg. 188: 611–622 (1978).

19. "Do-It-Yourself" Fibrin Glue, News Bulletin-/American College of Surgeons, pg. 8, February 1984.

What is claimed is:

1. A method of preparing a fibrin glue useful in surgical procedures which comprises:
   (a) preparing a cryoprecipitated suspension containing fibrinogen and Factor XIII by freezing fresh frozen plasma from a single donor which has been screened for blood transmitted diseases at about $-80°$ C. for at least about 6 hours, raising the temperature of the frozen plasma so as to form a supernatant and a cryoprecipitated suspension containing figrinogen and Factor XIII, and recovering the cryoprecipitated suspension;
   (b) applying a defined volume of the suspension to a desired site; and
   (c) applying a composition containing a sufficient amount of thrombin to the site so as to cause the fibrinogen in the suspension to be converted to the fibrin glue which then solidifies in the form of a gel.

2. A method of claim 1, wherein the thrombin is derived from a human or other animal.

3. A method of claim 2, wherein the animal is a cow, sheep or pig.

4. A method of claim 1, wherein the composition also contains a suitable amount of an anti-fibrinolytic substance.

5. A method of claim 4, wherein the anti-fibrinolytic substance is aprotinin.

6. A method of claim 1, wherein the composition also contains a suitable amount of an appropriate calcium salt.

7. A method of claim 1, wherein the suspension and the composition containing thrombin are applied to the site in a surgically acceptable vehicle.

8. A method of claim 7, wherein the vehicle comprises a gel.

9. A method of claim 7, wherein the vehicle comprises a stretched fabric.

10. A fibrin glue prepared by the method of claim 1.

11. A fibrin glue in a gel vehicle prepared by the method of claim 9.

12. A fibrin glue kit for use in providing hemostasis during surgery which comprises a cryoprecipitated suspension containing fibrinogen and Factor XIII prepared by freezing fresh frozen plasma from a single donor which has been screened for blood transmitted diseases at about $-80°$ C. for at least about 6 hours, raising the temperature of the frozen plasma so as to form a supernatant and a cryoprecipitated suspension containing fibrinogen and Factor XIII, and recovering the cryoprecipitated suspension and a composition containing thrombin.

13. A kit of claim 12, wherein the composition containing thrombin contains a suitable amount of an anti-fibrinolytic substance.

14. A kit of claim 13, wherein the anti-fibrinolytic substance comprises aprotinin.

15. A kit of claim 12, wherein the composition containing thrombin also contains a suitable amount of an appropriate calcium salt.

16. A kit of claim 12 which further comprises a surgically acceptable vehicle for the fibrin glue.

17. A kit of claim 16, wherein the vehicle is a gel.

18. A kit of claim 12 which further comprises at least one synthetic vascular patch.

19. A kit of claim 12 which further comprises at least one synthetic vascular graft.

20. A method of claim 1, wherein the donor is a human or other animal.

21. A method of claim 20, wherein the donor is a cow, sheep or pig.

* * * * *